(12) United States Patent
Thomas et al.

(10) Patent No.: US 12,201,544 B2
(45) Date of Patent: Jan. 21, 2025

(54) PERINEAL BANDAGE FOR VAGINAL DELIVERY

(71) Applicant: Intermountain Intellectual Asset Management, LLC, Salt Lake City, UT (US)

(72) Inventors: Andrew Perry Thomas, Pleasant Grove, UT (US); Jon Edward Beck, Salt Lake City, UT (US)

(73) Assignee: Intermountain Intellectual Asset Management, LLC, Salt Lake City, UT (US)

( * ) Notice: Subject to any disclaimer, the term of this patent is extended or adjusted under 35 U.S.C. 154(b) by 0 days.

(21) Appl. No.: 17/820,422

(22) Filed: Aug. 17, 2022

(65) Prior Publication Data

US 2023/0055793 A1 Feb. 23, 2023

Related U.S. Application Data

(60) Provisional application No. 63/236,102, filed on Aug. 23, 2021.

(51) Int. Cl.
*A61F 5/00* (2006.01)
*A61B 17/42* (2006.01)
(Continued)

(52) U.S. Cl.
CPC ............ *A61F 5/0093* (2013.01); *A61F 13/02* (2013.01); *A61B 17/42* (2013.01); *A61F 2013/00544* (2013.01)

(58) Field of Classification Search
CPC ......... A61L 15/58; A61B 17/42; A61B 17/08; A61F 5/0093; A61F 13/02;
(Continued)

(56) References Cited

U.S. PATENT DOCUMENTS

| 4,520,807 A | 6/1985 | Rotter |
| 5,891,074 A | 4/1999 | Cesarczyk |

(Continued)

FOREIGN PATENT DOCUMENTS

| AU | 2009214020 B2 | 7/2014 |
| WO | 2018130917 A1 | 7/2018 |
| WO | 2019195097 A1 | 10/2019 |

OTHER PUBLICATIONS

Product Insert for Hem-Avert Perianal Stabilizer, PB-RRF-001 Rev. J, Jan. 2, 2017, 4 pages, Jan. 2, 2017, 4.
(Continued)

*Primary Examiner* — Caitlin A Carreiro
(74) *Attorney, Agent, or Firm* — Dorsey & Whitney LLP (57) ABSTRACT

A perineal bandage for preventing and treating tears that occur during childbirth. The perineal bandage includes a flexible bandage having a first side and a second side, wherein the second side includes an adhesive configured to adhere the bandage to the skin of a patient. The perineal bandage may further include a plurality of tearing zones that tear before the bandage. The perineal bandage may further include a reinforced region disposed along a portion of a bottom edge of the bandage, wherein the reinforced region requires a greater amount of force to tear than the bandage and the tearing zones.

17 Claims, 4 Drawing Sheets

(51) Int. Cl.
*A61F 13/00* (2024.01)
*A61F 13/02* (2024.01)

(58) Field of Classification Search
CPC .. A61F 13/0246; A61F 13/0259; A61F 13/00; A61F 13/00008; A61F 13/00021; A61F 13/15; A61F 2013/00544; A61F 2013/00561; A61F 2013/00574; A61F 2013/00591; A61F 2013/00595; A61F 2013/00089; A61F 2013/00582; A61F 2013/16
USPC .......... 602/41, 54, 58, 60, 67; 424/445, 448; 606/119, 215; 604/358
See application file for complete search history.

(56) References Cited

U.S. PATENT DOCUMENTS

| | | | |
|---|---|---|---|
| 7,673,633 B2 | 3/2010 | Blurton et al. | |
| 8,657,836 B2 | 2/2014 | Haadem | |
| 2004/0242097 A1* | 12/2004 | Hasenoehrl | A44B 18/0011 442/361 |
| 2005/0283050 A1 | 12/2005 | Gundlapalli et al. | |
| 2007/0282238 A1* | 12/2007 | Madsen | A61F 13/023 602/57 |
| 2009/0148503 A1* | 6/2009 | Trieu | A61B 17/42 424/447 |
| 2015/0257939 A1* | 9/2015 | Ficchi | A61F 13/105 602/43 |
| 2015/0313636 A1 | 11/2015 | Shen et al. | |
| 2020/0315659 A1 | 10/2020 | Heinberg | |

OTHER PUBLICATIONS

Lavesson, Tony , et al., Lavesson et al., "A perineal protection device designed to protect the perineum during labor: a multicenter randomized controlled trial", European Journal of Obstetrics & Gynecology and Reproductive Biology 181 (2014) 10-14, 5 pages, Jul. 20, 2014, 5.

* cited by examiner

FIG. 6

PERINEAL BANDAGE FOR VAGINAL DELIVERY

RELATED APPLICATIONS

This application claims priority to U.S. Provisional Patent Application No. 63/236,102, filed Aug. 23, 2021, and titled PERINEAL BANDAGE FOR VAGINAL DELIVERY, which is incorporated herein by reference in its entirety.

TECHNICAL FIELD

The present disclosure relates generally to the field of medical devices and methods for assisting a mother during the delivery of a child. More particularly, some embodiments relate to medical devices, in particular topical devices, for protection against tissue tears of the perineal, anus, and vagina of a pregnant mother during delivery of a child.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

There are about 140 million births worldwide per year. A majority of these births are vaginal delivery, at least 100 million per year. In the United States, there are about 2.6 million births per year. The majority of these births are vaginal delivery, at least 1.4 million per year. Worldwide, about 40% of mothers' perineal tissue tear during vaginal delivery and about 90% of first time mothers' perineal tissue tear during vaginal delivery.

Perineal tearing is a complication that a pregnant mother faces during childbirth. Delivery can lead to overstretching of the vagina, causing tears in the perineal tissue between the vagina and the rectum, as the vagina of the mother stretches to accommodate the passage of the baby's body through the birth canal. In some instances, an episiotomy is performed as a prophylactic measure to prevent uncontrolled tearing between the vagina and the anus. However, current trends are moving away from the use of episiotomies as a prophylactic measure for tearing.

Perineal tears or lacerations are typically classified to indicate the severity of the trauma to the perineum, as follows:

First degree tear: laceration is limited to the fourchette and superficial perineal skin or vaginal mucosa.

Second degree tear: laceration extends beyond the fourchette, perineal skin, and vaginal mucosa to perineal muscles and fascia, but not the anal sphincter.

Third degree tear: the fourchette, perineal skin, vaginal mucosa, muscles, and anal sphincter are torn. Third degree tears are further characterized as "3a," "3b," and "3c," where 3a is characterized by a partial tear of the external anal sphincter involving less than 50% thickness, 3b is characterized by a greater than 50% tear of the external anal sphincter, and 3c is characterized by the internal sphincter being torn.

Fourth degree tear: the fourchette, perineal skin, vaginal mucosa, muscles, sphincter, and rectal mucosa are torn.

In a 2015 study of 7 million mothers, 3.3% of the women had a third degree tear and 1.1% of the women had a fourth degree tear. Such tearing can cause significant post-delivery complications for the mother. As a result, there has long been a need to reduce the rate and nature of perineal tears without hindering or preventing the vaginal stretching needed to facilitate delivery.

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

The phrase "coupled to" is broad enough to refer to any suitable coupling or other form of interaction between two or more entities, including mechanical, and thermal interaction. Thus, two components may be coupled to each other even though they are not in direct contact with each other.

The terms "proximal" and "distal" are opposite directional terms. For example, the distal end of a device or component is the end of the component that is furthest from the practitioner during ordinary use. The proximal end refers to the opposite end, or the end nearest the practitioner during ordinary use.

Figure 1:
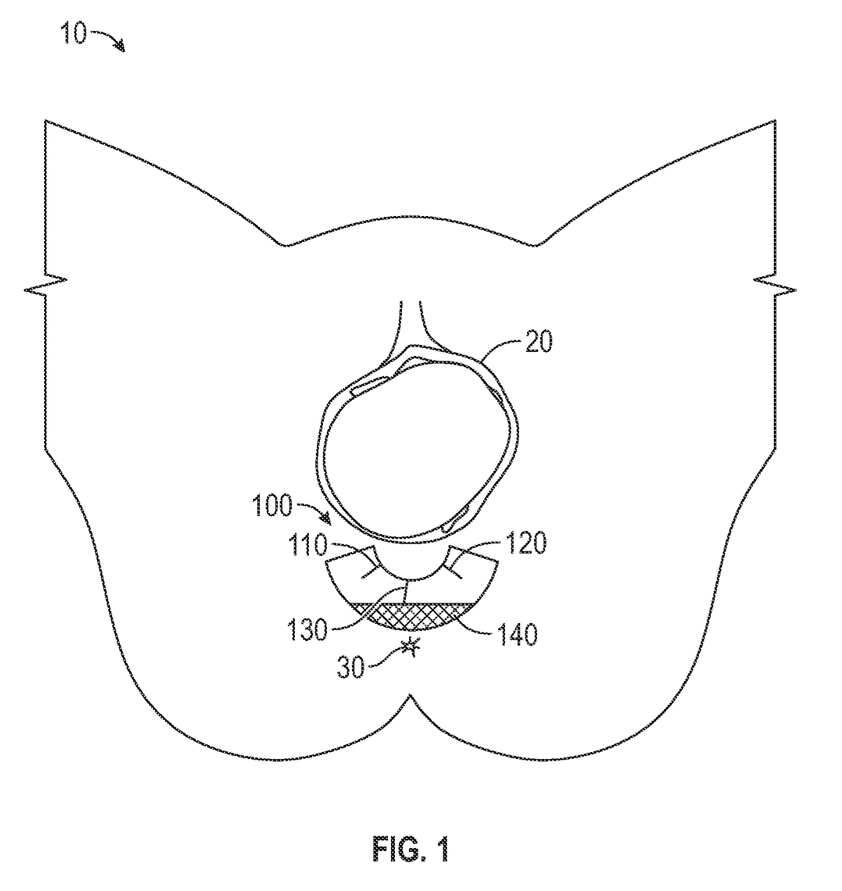
FIG. 1 illustrates a perineal bandage adhered to the perineal tissue between the vagina and the anus of a patient.
Figure 2A:
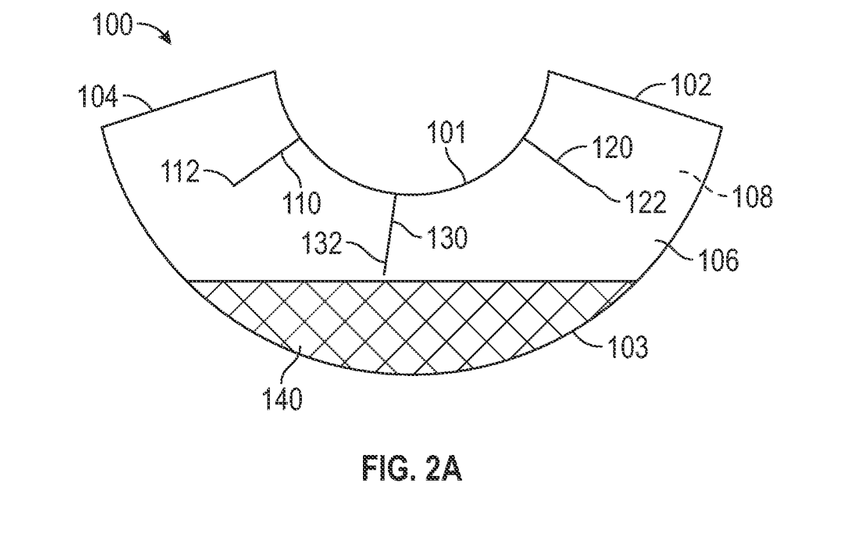
FIG. 2A illustrates a detailed view of the perineal bandage of FIG. 1 depicting the tear zones prior to tearing.
Figure 2B:
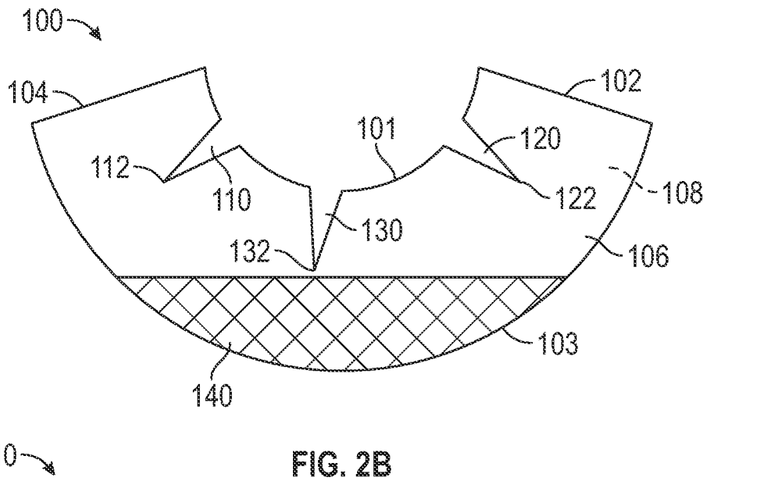
FIG. 2B illustrates a detailed view of the perineal bandage of FIG. 1 depicting the tear zones after tearing.

FIG. 1 illustrates an embodiment of a perineal bandage 100 applied to a patient 10. The perineal bandage 100 is coupled or adhered to skin and the perineal tissue between the vagina 20 and the anus 30. FIG. 2A illustrates a detailed view of the perineal bandage 100 depicting tear zones 110, 120, 130 prior to tearing. FIG. 2B illustrates a detailed view of the perineal bandage 100 depicting tear zones 110, 120, 130 after tearing.

The perineal bandage 100 comprises a substantially U-shape. As further detailed below, other shapes and/or sizes are also contemplated. The perineal bandage 100 may comprise a first edge 101, a second edge 102, a third edge 103, and a fourth edge 104. The perineal bandage 100 may comprise a first side 106 (outer side) and a second side 108 (inner side). The perineal bandage 100 may be fabricated from one or more of fabric, plastic, or any other suitable material. The perineal bandage 100 may be waterproof, water-resistant, breathable, partly-porous, etc.

The perineal bandage 100 can also be flexible and/or stretchable. For instance, the perineal bandage 100 can be configured to flex and/or stretch to accommodate the flexing and/or stretching of the patient during childbirth. More specifically, the perineal bandage 100 can be configured to flex and/or stretch to accommodate the flexing and/or stretching of the perineal tissue (and surrounding tissue) of the patient during childbirth. In some instances, the perineal bandage 100 comprises a flexibility and/or stretchability that is substantially the same as the flexibility and/or stretchability of the perineal tissue (and surrounding tissue) of a patient. In such instances, the perineal bandage 100 can flex and/or stretch with the patient up to a certain threshold, after which the perineal bandage 100 can be configured to tear along tear zones 110, 120, 130 further discussed below.

The second side 108 may comprise an adhesive for attaching the perineal bandage 100 to the skin of the patient 10 when the second side 108 comes in direct contact with the skin of the patient 10. In some embodiments, the adhesive is a pressure sensitive adhesive. The pressure sensitive adhesive may include rubbers, acrylate, and silicone formulations. Additional types of adhesives include acrylics or cyanoacrylates, silicone, and polyurethanes. The adhesive can also include karaya gum and/or derivatives thereof. In some embodiments, the adhesive includes hydrophilic materials that are compliant with wet environments. In particular embodiments, the hydrophilic materials can absorb water into their matrix without losing their adhesive properties. In more particular embodiments, the hydrophilic materials can increase their adhesiveness upon the absorption of water. In some embodiments, the second side 108 comprises an backing that may be removed to expose the adhesive before adhering or coupling the perineal bandage 100 to the patient 10.

Figure 5:
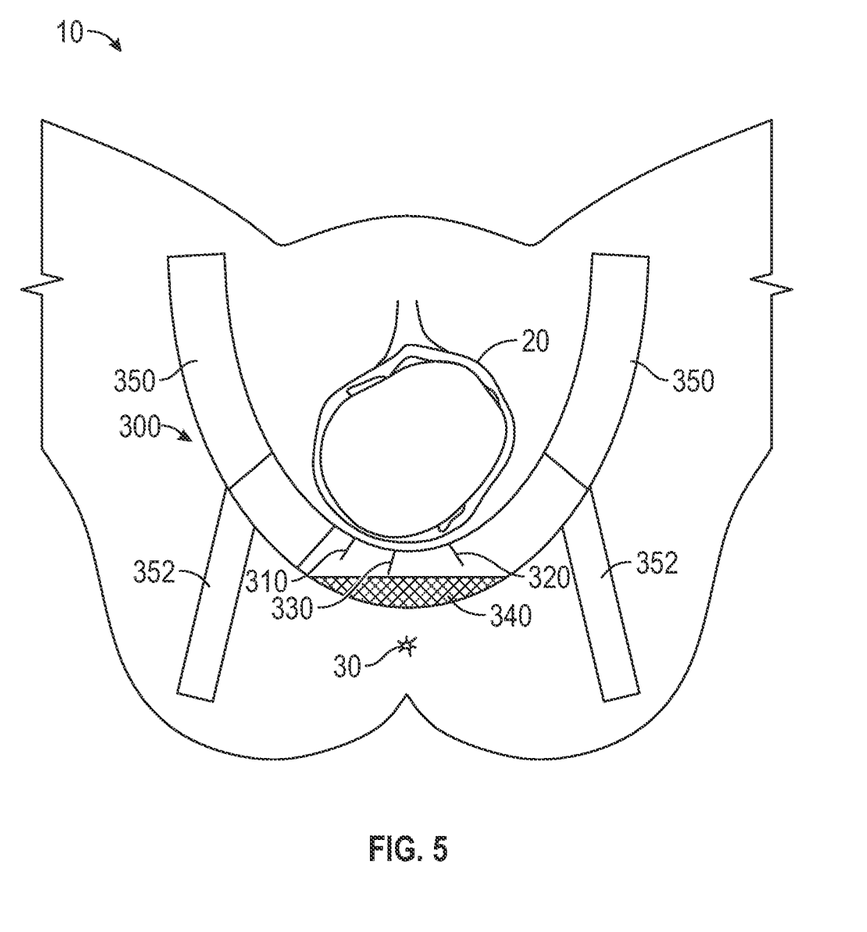
FIG. 5 illustrates another perineal bandage adhered to the perineal tissue between the vagina and the anus of a patient.

The perineal bandage 100 may come in a variety of different sizes. The variety of different sizes may enable a medical professional to select the size that would be most appropriate for the patient 10. The perineal bandage 100 may also come in a variety of different shapes. For example, the perineal bandage 100 could be V-shaped, rectangular, triangular, polygonal, circular, elliptical, diamond-shaped, and the like. One or more anchors or extension members may also be included as shown in FIG. 5 and detailed below.

The perineal bandage 100 provides additional support to the perineal tissue to prevent it from tearing. However, in some childbirths, tearing may be unavoidable, even with the additional support provided by the perineal bandage 100. In these circumstances, the perineal bandage 100 is configured to direct the tearing in certain directions to help avoid serious tears, such as tears along a centerline from the vagina 20 to the anus 30.

To help direct the tearing, the perineal bandage 100 may comprise one or more tearing zones 110, 120, 130. The tearing zones 110, 120, and 130 would require a predetermined amount of force before the tearing zones 110, 120, and 130 would tear. For example, tearing zone 110 may be a primary tearing zone and may require the least amount of force before the tearing zone 110 would tear. Tearing zone 120 may be a secondary tearing zone and may require more force than the primary zone before the tearing zone 120 would tear. Tearing zone 130 may be a tertiary tearing zone and may require the most amount of force of the tearing zone 110, 120, and 130 before tearing zone 130 would tear. In other words, the primary tearing zone 110 is configured to tear with the least amount of force compared to the other tearing zones 120 and 130, the tertiary tearing zone 130 is configured to tear with the most amount of force compared to the other tearing zones 110 and 120, and the second tearing zone 120 is configured to tear with a force between the primary tearing zone 110 and the tertiary tearing zone 130. More or less than three tearing zones 110, 120, 130 may also be used.

During use, the bandage 100 can first stretch with the patient and perineal tissue. After a threshold force or stretch is achieved, a first tear zone 110 may give way and tear. Subsequent tear zones 120, 130 may give way and tear after subsequent threshold forces or stretches are achieved, depending on the number of tear zones 110, 120, 130, that are used. For instance, after a second threshold force or stretch is achieved, a second tear zone 120 may give way and tear. And after a third threshold force or stretch is achieved, a third tear zone 130 may give way and tear, etc.

The tearing zones 110, 120, and 130 may be formed in a number of different ways. For example, each tearing zone 110, 120, and 130 may be fabricated from a different material. In some embodiments, the tearing zones 110, 120, and 130 are fabricated from a different material than the rest of the perineal bandage 100. In some embodiments, each of the tearing zones 110, 120, and 130 may have a different thickness or a different number of layers. In some embodiments, each of the tearing zones 110, 120, and 130 may have a localized region of weakness. For example, each of the tearing zones 110, 120, an 130 can include a different degree of perforations or tear lines. In some embodiments, the tearing zones 110, 120, and 130 may comprise a combination of the above-noted features. In some instances, the tearing zones may have a removable tape, piece, or layer to allow the zone's relative strength to be reduced during a delivery to facilitate tearing in that region at the discretion of the provider performing the delivery. If desired, the tear zones 110, 120, 130 can also include one or more different colors to visually show where the tear zones 110, 120, 130 are located.

In some embodiments, the bandage 100 is a multilayer structure or laminate. In such embodiments, each layer can comprise different materials, thicknesses, and/or strength properties. For instance, an illustrative multilayer structure can comprise first, second, and third layers, each of which can comprise different materials or thicknesses. The first layer can be configured to stretch to a first predetermined tensile load, after which the first layer will tear. The second layer can be configured to stretch to a second predetermined tensile load (which is greater than the first predetermined tensile load), after which the second layer will tear. The third layer can be configured to stretch to a third predetermined tensile load (which is greater than the second predetermined tensile load), after which the third layer will tear. Additional layers can also be used. The first, second, and third layers can also be arranged or layered (e.g., with slits, perforations, or layer breaks) such that the tears are directed along the tear zones 110, 120, 130 as desired.

In the illustrated embodiment, the primary tearing zone 110 is disposed to the left, the secondary tearing zone 120 is disposed to the right, and the tertiary tearing zone 130 is disposed between the primary tearing zone 110 and the secondary tearing zone 120. In some embodiments, the tearing zones 110, 120, and 130 may be disposed in different locations than the illustrated embodiment. In some embodiments, there may be more or less than three tearing zones as illustrated. For example, in some embodiments, there may be one or two tearing zones, in other embodiments there may be five or more. Further, in the illustrated embodiment, a tearing zone (e.g., tertiary tearing zone 130) is offset from the centerline between the vagina 20 and the anus 30, thereby directing tears away from this centerline. In other embodiments, a tearing zone (e.g., a tertiary tearing zone 130) can be disposed along the centerline between the vagina 20 and the anus 30 that is configured to limit and/or control the length of a tear along the centerline.

The tearing zones 110, 120, and 130 may have a specific shape to direct the tearing. For example, the tearing zones 110, 120, and 130 may have a linear or triangular shape. The tearing zones 110, 120, and 130 may extend from the first edge 101 toward the third edge 103. In some instances, the width of the tearing zones becomes smaller as it extends from the first edge 101 toward the third edge 103. In the illustrated embodiment, the tearing zones 110, 120, and 130 extend about halfway between the first edge 101 and the third edge 103. The tensile strength of the tearing zones 110, 120, and 130 may progressively increase as the tearing zones 110, 120, and 130 extend from the first edge 101 toward the third edge 103. For example, the thickness of each tearing zone 110, 120, and 130 may progressively increase from the first edge 101 toward the third edge 103.

The positioning of the tertiary tearing zone 130 (e.g., the strongest tearing zone) may be placed closer to the centerline between the vagina 20 and the anus 30. The tertiary tearing zone 130 may not follow the centerline exactly, but may be slightly offset from the centerline to help prevent tearing along the centerline itself. In other words, an end 132 of the tertiary zone 130 is not disposed along the centerline.

The tearing zones 110 and 120 may also be disposed to not point from the vagina 20 toward the anus 30. An end 112 of the tearing zone 110 may be directed at an angle away from the centerline between the vagina 20 and the anus 30. An end 122 of the tearing zone 120 may be directed at an angle away from the centerline between the vagina 20 and the anus 30. Accordingly, if the mother tears during childbirth, the mother would tear first along the primary tearing zone 110, then along the secondary tearing zone 120 before tearing along the tertiary tearing zone 130.

In some embodiments, the perineal bandage 100 may comprise a plurality of positioning lines (not shown) disposed on the first side 106 to help the medical practitioner place the perineal bandage. The perineal bandage may be placed before or during childbirth. The perineal bandage 100 may comprise a centerline positioning line to align the perineal bandage along the centerline between the vagina 20 and the anus 30. These positioning lines are helpful to ensure proper placement of the perineal bandage 100 by the medical practitioner. If the perineal bandage 100 is placed before or during childbirth, the perineal bandage 100 may help prevent, alleviate, and/or attenuate the severity of tears that may occur during childbirth. The positioning lines may also help the medical practitioner line up torn tissue during repair. The tears that result due to childbirth may also be supported by the perineal bandage 100 in such a way as to aid in the repair of the tissue.

The tertiary tearing zone 130 requires the most amount of force of the plurality of tearing zones 110, 120, and 130 before tearing. Accordingly, the tertiary tearing zone 130 may reinforce the skin and perineal tissue closer to or along the centerline between the vagina 20 and the anus 30. In some embodiments, the tertiary tearing zone 130 may be reinforced. Additional reinforcing material can be applied to the bandage after placement at the discretion of the delivering provider if it is perceived additional support is needed. For instance, this can be done with additional adhesive material that could be placed atop of the bandage before or after application of the perineal bandage.

The perineal bandage 100 may further comprise a reinforced region 140. The reinforced region 140 may be disposed along a portion of the third edge 103. The reinforced region 140 may be disposed below the end 132 of the tertiary tearing zone 130. The reinforced region 140 requires a greater amount of force to tear than the rest of the perineal bandage 100, including the tearing zones 110, 120, and 130. The reinforced region 140 is configured to help prevent third and fourth degree tears. As discussed above, third and fourth degree tears involve the tearing of the anal sphincter. The reinforced region 140 may be reinforced with fibers. The fibers may be high strength, high modulus fibers for increasing the strength of the reinforced region 140 of the perineal bandage 100. This region may be reinforced with thicker material, a different material, or a plurality of materials. It may also include horizontal tension lines that would prevent tearing in this region. If desired, the reinforced region 140 can also include one or more different colors to visually show where the reinforced region 140 is located on the bandage 100.

With specific reference to FIG. 2A, a bandage 100 is depicted prior to tearing of the tear zones 110, 120, 130. As shown therein, the tear zones 110, 120, 130 are linear lines that are configured to give way or otherwise tear as threshold forces are achieved. FIG. 2B depicts a bandage 100 showing the tear zones 110, 120, 130 after being torn or otherwise opened. As shown therein, the tear zones 110, 120, 130 are opened and stop at the ends 112, 122, 132 of the tear zones 110, 120, 130. As can be appreciated, the tear zones 110, 120, 130 can be configured to help control both the direction and length of any tissue tearing during childbirth.

Figure 3:
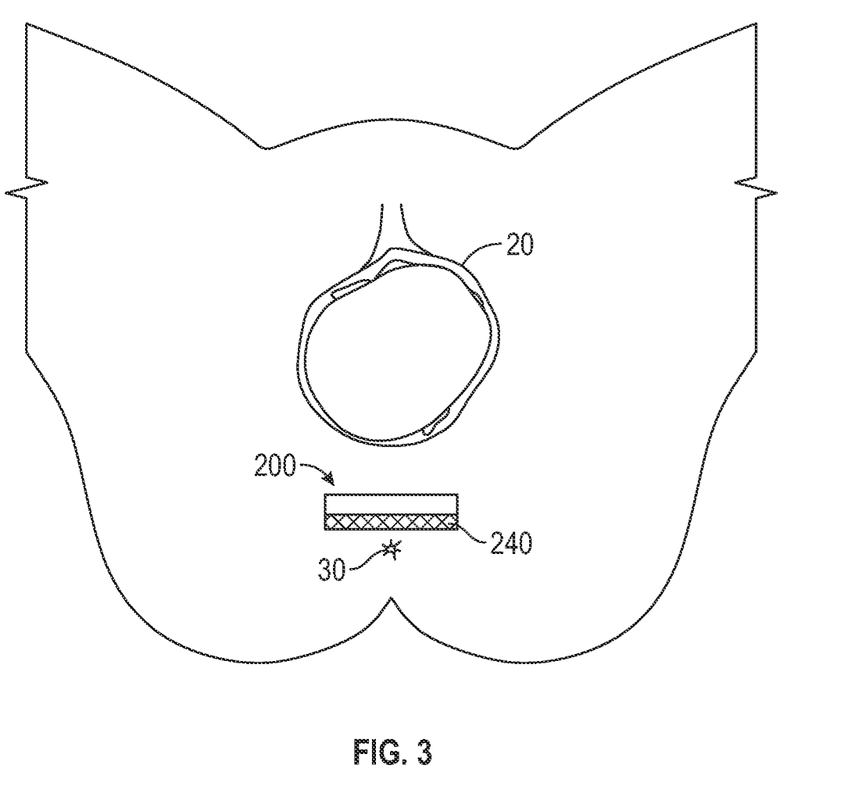
FIG. 3 illustrates a perineal bandage adhered to the perineal tissue between the vagina and the anus of a patient.

FIG. 3 depicts an embodiment of a perineal bandage 200 that resembles the perineal bandage 100 described above in certain respects. Accordingly, like features are designated with like reference numerals, with the leading digits incremented to "2." For example, the embodiment depicted in FIGS. 3-4 includes a reinforced region 240 that may, in some respects, resemble the reinforced region 140 of FIGS. 1-2A-2B. Relevant disclosure set forth above regarding similarly identified features thus may not be repeated hereafter. Moreover, specific features of perineal bandage 100 and related components shown in FIGS. 1-2A-2B may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the perineal bandage 200 and related components depicted in FIGS. 3-4. Any suitable combination of the features, and variations of the same, described with respect to the perineal bandage 100 and related components illustrated in FIGS. 1-2A-2B can be employed with the perineal bandage 200 and related components of FIGS. 3-4, and vice versa. This pattern of disclosure applies equally to further embodiments depicted in subsequent figures and described hereafter, wherein the leading digits may be further incremented.

Figure 4:
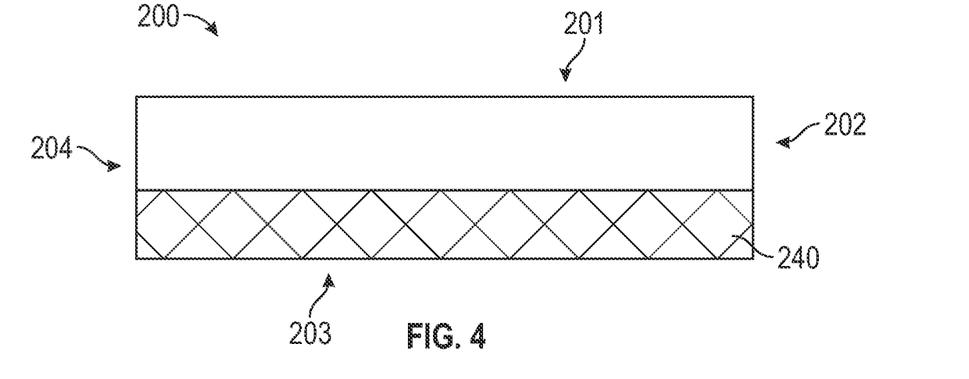
FIG. 4 illustrates a detailed view of the perineal bandage of FIG. 3.

FIG. 3 illustrates an embodiment of the perineal bandage 200 applied to a patient 10. The perineal bandage 200 is coupled or adhered to skin and the perineal tissue between the vagina 20 and the anus 30. FIG. 4 illustrates a detailed view of the perineal bandage 200.

The perineal bandage 200 comprises a rectangular shape, although other shapes can also be used, including rectangular, triangular, polygonal, diamond shaped, circular, elliptical, and the like. The perineal bandage 200 may comprise a first edge 201, a second edge 202, a third edge 203, and a fourth edge 204. The perineal bandage 200 may comprise a first side 206 (outer side) and a second side 208 (inner side). The second side 208 may comprise an adhesive for attaching the perineal bandage 200 to the skin of the patient 10 when the second side 208 comes in direct contact with the skin of the patient 10.

While not illustrated, the perineal bandage 200 may comprise one or more tearing zones similar to the tearing zones discussed above.

The perineal bandage 200 may further comprise a reinforced region 240. The reinforced region 240 may be disposed along the third edge 203. The reinforced region 230 may comprise a bottom third of the perineal bandage 200. The reinforced region 240 is configured to help prevent third and fourth degree tears. As discussed above, third and fourth degree tears involve the tearing of the anal sphincter. The reinforced region 240 may be reinforced with fibers. The fibers may be high strength, high modulus fibers for increasing the strength of the reinforced region 240 of the perineal bandage 200. This can be done with a different material with a higher tensile strength, combination of material, or material of varied thicknesses.

FIG. 5 illustrates another embodiment of a perineal bandage 300 applied to a patient 10. The bandage 300 is coupled or adhered to skin and the perineal tissue between the vagina 20 and the anus 30. As shown in FIG. 5, the bandage 300 includes tear zones 310, 320, 330 and a reinforced region 340, similar to those described above with regards to FIGS. 1-2B. The bandage 300 further includes one or more anchoring or extension members 350, 352 to aid in anchoring the bandage 300 to the patient 10. In particular, the bandage 300 includes extension members 350 that are configured to anchor or adhere the bandage 300 to the thigh regions of the patient 10. The bandage 300 also includes extension members 352 that are configured to anchor or adhere the bandage 300 to the buttock regions of the patient 10. Additional types, sizes, and/or shapes of anchoring or extension members may also be used.

Figure 6:
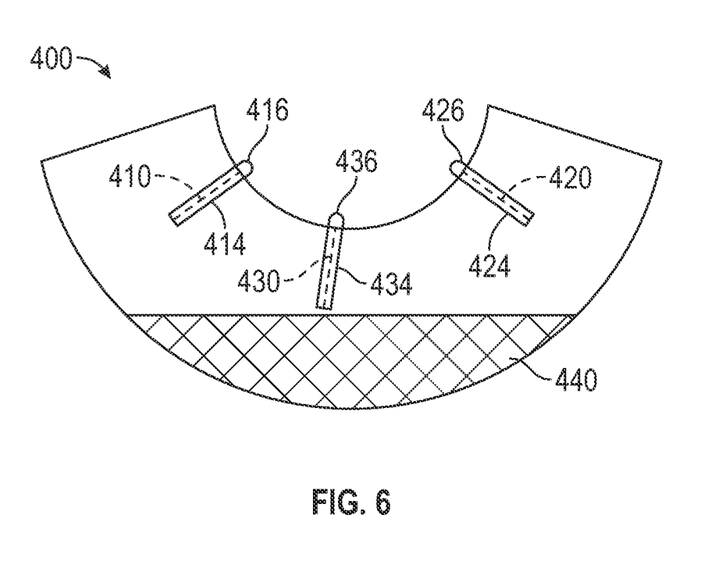
FIG. 6 illustrates another perineal bandage.

FIG. 6 illustrates another embodiment of a perineal bandage 400. As shown in FIG. 6, the bandage 400 includes tear zones 410, 420, 430 and a reinforced region 440, similar to those described above with regards to FIGS. 1-2B. The bandage 400 further includes removable tape or strips of material 414, 424, 434 that allows each tear zone's relative strength to be reduced during a delivery to facilitate tearing in that region at the discretion of the clinician performing the delivery. In other words, tearing at the tear zones 410, 420, 430 can be at least partially clinician-controlled. In some of such embodiments, each removable tape or strip of material 414, 424, 434 includes a tab 416, 426, 426 that can be grasped and pulled by the clinician to remove the tape or strip of material 414, 424, 434 thus enabling the tear zone's 410, 420, 430 to be torn. In other embodiments, the bandage 400 includes a multi-layer structure or laminate wherein one or more layers can be removed to enable tearing at the tear zone 410, 420, 430 (similar to the removal of the tape or strip of material 414, 424, 434).

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

The invention claimed is:

1. A perineal bandage comprising: a bandage comprising a first side and a second side, wherein the bandage is flexible and the second side comprises an adhesive configured to adhere the bandage to the skin of a patient; a reinforced region disposed along a portion of a bottom edge of the bandage, wherein the reinforced region requires a greater amount of force to tear than unreinforced regions of the bandage; and one or more tearing zones having a base disposed at a top edge of the bandage and extending partially towards the bottom edge of the bandage, wherein the one or more tearing zones are positioned and configured to direct tearing of the bandage at an angle away from a center of the bandage, wherein the one or more tearing zones further comprise a primary tearing zone, a secondary tearing zone, and a tertiary tearing zone, wherein the tertiary tearing zone is disposed near and offset from a center of the top edge of the bandage such that no tearing zone is disposed on the center of the bandage.

2. The perineal bandage of claim 1, wherein the primary tearing zone is configured to tear with the least amount of force compared to other tearing zones, the tertiary tearing zone is configured to tear with the most amount of force compared to other tearing zones, and the secondary tearing zone is configured to tear with a force between the primary tearing zone and the tertiary tearing zone.

3. The perineal bandage of claim 2, wherein the primary tearing zone is disposed to one side of the tertiary tearing zone and the secondary tearing zone is disposed to the opposite side of the tertiary tearing zone as the primary tearing zone.

4. The perineal bandage of claim 1, wherein the bandage is configured to be placed on perineal tissue of the patient.

5. The perineal bandage of claim 4, wherein the bandage comprises a flexibility that is configured to flex and stretch with the perineal tissue.

6. The perineal bandage of claim 1, wherein the bandage is substantially U-shaped.

7. The perineal bandage of claim 1, wherein the bandage is rectangular, diamond shaped, elliptical, or circular.

8. The perineal bandage of claim 1, wherein the bandage is configured to be adhered to perineal tissue of the patient with an adhesive, wherein the adhesive comprises a hydrophilic adhesive.

9. The perineal bandage of claim 1, wherein the bandage comprises one or more extension members configured to anchor the bandage to a thigh or buttocks region of the patient.

10. The perineal bandage of claim 1, wherein the bandage comprises a multilayer laminate structure comprising a first layer, a second layer, and a third layer, wherein the first layer is configured to tear at a first tensile load, the second layer is configured to tear at a second tensile load, and the third layer is configured to tear at a third tensile load.

11. The perineal bandage of claim 1, wherein the bandage comprises a removable strip disposed at each of the one or more tearing zones, wherein removal of the removable strip enables the tearing zone to tear.

12. A perineal bandage comprising: a bandage comprising a first side and a second side, wherein the bandage is flexible and the second side comprises an adhesive configured to adhere the bandage to skin of a patient; a reinforced region disposed along a portion of a bottom edge of the bandage, wherein the reinforced region requires a greater amount of force to tear than unreinforced regions of the bandage; and one or more tearing zones having a base disposed at a top edge of the bandage opposite to the bottom edge of the bandage and extending partially towards the bottom edge, wherein the one or more tearing zones are configured to be an initial tear region of the bandage, at least one tearing zone of the one or more tearing zones being oriented at a non-perpendicular angle relative to a top edge of the reinforced region and being disposed near and offset from a center of a top edge of the bandage such that no tearing zone is disposed on the center of the bandage.

13. The perineal bandage of claim 12, wherein the one or more tearing zones further comprises a primary tearing zone and a secondary tearing zone both offset from a center of the top edge of the bandage, wherein the primary tearing zone is configured to tear with less force compared to the secondary tearing zone.

14. The perineal bandage of claim 13, wherein the bandage further comprises a tertiary tearing zone disposed near and offset from the center of the top edge of the bandage between the primary tearing zone and the secondary tearing zone, wherein the primary tearing zone is configured to tear with the least amount of force compared to other tearing zones, the tertiary tearing zone is configured to tear with the most amount of force compared to other tearing zones, and the secondary tearing zone is configured to tear with a force between the primary tearing zone and the tertiary tearing zone.

15. The perineal bandage of claim 12, wherein the bandage comprises a removable strip disposed at each tearing zone of the one or more tearing zones, wherein removal of the removable strip enables the tearing zone to tear.

16. A perineal bandage configured to be placed on perineal tissue of a patient, comprising: a bandage comprising a first side and a second side, wherein the bandage is flexible and the second side comprises an adhesive configured to adhere the bandage to skin of the patient; and a reinforced region disposed along a portion of a bottom edge of the bandage, wherein the reinforced region requires a greater amount of force to tear than unreinforced regions of the bandage, wherein the bandage comprises a plurality of tearing zones each having a base disposed at a top edge of the bandage and extending partially towards the bottom edge of the bandage and disposed at an angle away from a center of the bandage, wherein the plurality of tearing zones are configured to control tearing of the bandage when the bandage is placed on the perineal tissue of the patient, wherein the plurality of tearing zones comprises a primary tearing zone, a secondary tearing zone, and a tertiary tearing zone wherein the primary tearing zone is configured to tear with less force compared to at least one of the secondary tearing zone or the tertiary tearing zone, wherein the tertiary tearing zone is disposed near and offset from a center of a top edge of the bandage such that no tearing zone is disposed on the center of the bandage.

17. The perineal bandage of claim 16, wherein the primary tearing zone is configured to tear with the least amount of force compared to other tearing zones of the plurality of tearing zones, the tertiary tearing zone is configured to tear with the most amount of force compared to other tearing zones of the plurality of tearing zones, and the secondary tearing zone is configured to tear with a force between the primary tearing zone and the tertiary tearing zone.

* * * * *